United States Patent [19]

Froning

[11] 4,013,080
[45] Mar. 22, 1977

[54] CANNULA CONNECTOR AND DIRECTION INDICATOR MEANS FOR INJECTION SYSTEM

[76] Inventor: Edward C. Froning, 215 N. San Mateo Drive, San Mateo, Calif. 94401

[22] Filed: June 5, 1975

[21] Appl. No.: 584,103

Related U.S. Application Data

[63] Continuation-in-part of Ser. No. 511,655, Oct. 3, 1974, Pat. No. 3,941,127.

[52] U.S. Cl. .............................................. 128/347
[51] Int. Cl.² ........................................ A61B 17/34
[58] Field of Search ............... 128/215, 214.2, 347

[56] References Cited

UNITED STATES PATENTS

| | | | |
|---|---|---|---|
| 1,248,492 | 12/1917 | Hill | 128/347 |
| 2,794,435 | 6/1957 | Stevens | 128/214.2 |
| 3,608,539 | 9/1971 | Miller | 128/347 |
| 3,628,524 | 12/1971 | Jamshidi | 128/347 |
| 3,630,192 | 12/1971 | Jamshidi | 128/347 |
| 3,789,852 | 2/1974 | Kim et al. | 128/347 |

Primary Examiner—Lawrence W. Trapp
Attorney, Agent, or Firm—Julian Caplan

[57] ABSTRACT

A cannula has a hub formed at its proximal end with a terminal peripheral flange and also has a radial vane having an apertured proximal extension. A stylet fits into the cannula and has a hub with a skirt to receive the cannula hub flange and also having a hook received in the vane extension aperture to lock the two hubs together and insure protrusion of the stylet point from the distal end of the cannula. A barb on the hook latches the hubs together but is also used to disengage the hubs. An obturator has a hub and hook similar to the stylet. A disc-puncturing needle has a hub with an imperforate vane which is oriented with a bevel at the distal end of the needle and also provides leverage to connect the needle hub tightly to a Leur-lok or other fitting of a syringe. A tool comprises two leaves which can be pinched together to bend the distal of the needle to desired shape, the leaves being formed with complex curves so that a choice of bends is available. The apparatus is preferably used for injection into the nucleus pulposus of a lumbar disc of contrast fluids, probes and drugs.

10 Claims, 8 Drawing Figures

CANNULA CONNECTOR AND DIRECTION INDICATOR MEANS FOR INJECTION SYSTEM

This application is a continuation-in-part of Application Ser. No. 511,655, filed Oct. 3, 1974 and now U.S. Pat. No. 3,941,127.

This invention relates to a new and improved cannula connector and direction indicator means for injection system.

The present invention is particularly useful in lumbar disc puncture and assists the surgeon in locating the cannula and the various instruments which fit into the cannula for lateral disc puncture, especially for accomplishing the operation of chemonucleolysis. In that operation, diagnostic radiographic contrast fluids are injected into the nucleous pulposus and also fluids containing the enzyme chymopapain which, when injected into the nucleous pulposus, decompresses the disc, as discovered by Dr. Lyman Smith and set forth in U.S. Pat. No. 3,320,131. The apparatus is also useful for inserting probes in lumbar discs.

In accordance with the present invention, a cannula is provided in which is inserted a stylet to penetrate skin and muscle and then an obturator to isolate the nerve root crossing near the disc and bring the lumen of the cannula into direct contact with the disc and finally a fine caliber disc penetrating needle which is connected to a syringe through which fluids are injected into the nucleous pulposus.

Advantages of use of the apparatus in the procedure heretofore set forth are that the nerve roots lying in the target for lateral extra-canal approach are protected and the patient remains conscious during the operation so that the surgeon may communicate with the patient to assist in guiding the cannula and avoiding damage to the nerve root. The cannula serves as a sheath into which a plurality of other instruments may be installed, namely, the stylet, obturator and puncturing needle. All of these needles are kept out of the spinal canal and dura puncture is avoided.

A feature of the present invention is the provision of a bending tool which is easily manipulated by the surgeon to form a bend on the distal end of the needle of proper radius to reach the desired position for injection. The provision of a curve at the tip of the puncturing needle allows accurate maneuvering within the disc as well as outside the disc, as is sometimes necessary when the docking needle itself cannot be easily maneuvered past the nerve. By using the cannula as a "well casing" for the curved puncturing needle, it is possible to direct the puncturing needle to the disc, a task which would otherwise be extremely difficult in that the curvature of the needle would complicate immeasurably the maneuvering thereof.

A feature of the bending instrument is that varying radii may be formed with a single bending tool. The desired bend is dependent on several factors including the anatomy of the patient and the particular disc being penetrated. Thus, prebent needles are not as practical as a disposable, readily bendable needle which is fitted at the time of the operation to the needs of the particular injection.

A further feature of the invention is the provision of a vane extending radially from the hub of the needle aligned with the bevel on the end of the needle and also aligned with the curve on the needle which provides visible confirmation of the proper position of the needle. The vanes consistently align with the bevel to provide the surgeon constant awareness of the orientation even when the bevel is out of sight during continuing tissue passage.

The vanes of cannula and needle also preferably have indicia such as color coding and/or numerals so that the cannula is matched with the proper stylet, obturator and disc needle. These color codes or numbers also assist the surgeon in insuring that the proper fluids are injected in the proper discs by also matching the vane indicia of a needle with the disc perforated by its shaft. In addition, the indicia identify sets so as to avoid tolerance problems in the lengths of the various members.

Another advantage of the vanes is that they provide leverage assisting the surgeon in turning the various needles relative to each other and relative to the injection syringe, whereas the traditional hubs, smaller in size, do not afford the same purchase for rotation and locking.

Still another feature of the vane construction is that the cannula vane is formed with a perforation and the hub of the stylet and obturator are formed with hooks which fit through the perforation and each positively providing that the distal ends of the stylet and obturator protrude beyond the end of the cannula, avoiding the possibility of coring of nerve or other tissue by an open hollow cannula tip and providing positive visual confirmation within the portion of the cannula exposed when the leading end is out of sight under the skin deep in the tissue, a feature unavailable on the traditional hub. At the same time, a better grasp is provided for unlatching the hubs from each other when it is necessary to remove one of the same.

A further feature of the invention is the fact that the hub of the penetrating needle is provided with a vane which assists in connecting the Leur-lok fitting of an injection syringe to the hub of said needle and thus insures that the joint is tight, preventing escape of fluid. With the traditional Leur-lok type fit of hub and stylet or obturator, a false lock may occur in which the stylet or obturator is not fully seated. The vane facilitates connecting and disconnecting the syringe to the hub of the needle.

Other objects of the present invention will become apparent upon reading the following specification and referring to the accompanying drawings in which similar characters of reference represent corresponding parts in each of the several views.

Figure 1:
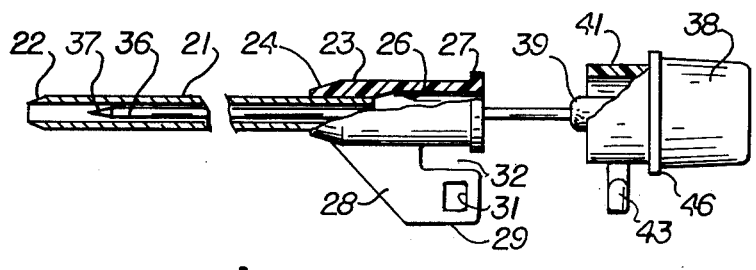
FIG. 1 is a side elevational view partly broken away in section showing a cannula and stylet in accordance with the present invention prior to complete assembly.

Cannula 21 is a thin walled instrument which serves as a "well casing" for the other instruments hereinafter described. Cannula 21 has a distal end 22 which is tapered and at the proximal end has a hub 23 shaped at its distal end indicated by reference numeral 24 to tightly engage the lumen at the upper end of cannula 21. Hub 23 is hollow and is formed with an opening 26 and the outer end is formed with a peripheral flange 27. Projecting radially outwardly of hub 23 is a thin vane 28 which is formed with an aperture 31. It will be noted that there is a gap 32 between extension 29 and barrel 26.

Figure 2:
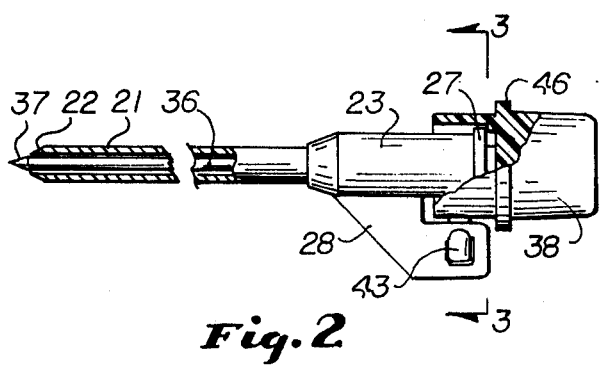
FIG. 2 is a view similar to FIG. 1 showing the two parts completely assembled.
Figure 3:
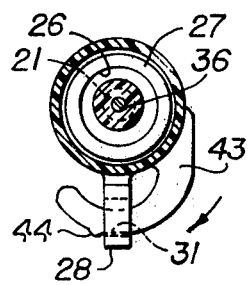
FIG. 3 is a sectional view taken substantially along the line 3—3 of FIG. 2.
Figure 6:
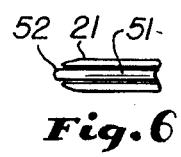
FIG. 6 is a fragmentary sectional view of a portion of the cannula of FIG. 1 and an obturator.
Figure 7:
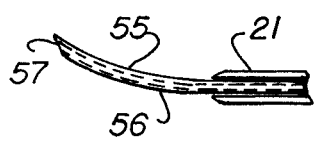
FIG. 7 is a view similar to FIG. 6 showing a disc needle.

The first instrument inserted in cannula 21 is stylet 36 which has a sharp point 37 at its distal end and is formed with a hub 38 at its proximal end. Hub 38 is hollow and has a connector 39 which is centrally located and fixed to the proximal end of stylet 36. Surrounding connector 39 is a skirt 41 to fit over flange 27. Extending radially from hub 38 is a curved hook 43, best shown in FIG. 3, which can be turned in a clockwise direction as viewed in FIG. 3 so that the end of the hook 43 penetrates aperture 31. A barb 44 is formed on hook 43 to lock with vane 28. There is sufficient flexibility to hook 43 so that when the surgeon turns the hub 38 relative to the hub 23 the barb 44 snaps behind vane 28 and holds the parts assembled. Nevertheless, when the surgeon wishes to disengage the two parts, by pulling up on the distal end of hook 43 the barb 44 may be disengaged, it being understood that the aperture 31 is of sufficient size to permit flexure of hook 43. When the hook 43 is engaged in the aparture 31, as shown in FIG. 2, the tip 37 of stylet 36 protrudes beyond the end 22 of cannula 21, the minimum protrusion consistent with acceptable manufacturing tolerances. This insures the proper placement of the stylet and prevents coring of nerve or other tissue which would occur if the stylet tip 37 were not fully extended. To facilitate turning of hub 38 relative to hub 23, a finger grip 46 is formed on the periphery of the hub 38. With the stylet 36 in place, the instrument can be used to penetrate skin, muscle and tissue to bring the tip 37 into proximity to the disc being treated.

After the stylet 37 has been projected to the desired point, the hub 38 is removed from flange 27 and the stylet is replaced with obturator 51 which has a blunt tip 52 which is less likely to damage the nerves or penetrate the dura. The surgeon can maneuver the obturator 52 into close proximity to or docking contact with the disc to be treated. A hub (not shown) similar in all respects to hub 38 is formed on the upper end of obturator 51. Preferably the hub on the upper end of obturator 51 is color coded or marked in some manner to distinguish from the hub 38 of stylet 36.

When the cannula 21 is in proximity to the disc to be treated, the obturator 51 is replaced with disc penetration needle 56. Such a needle is formed with a curve 55 by means hereinafter described or other means. The tip 57 of needle 56 is preferably beveled. At the proximal end of needle 56 is a hub 58 having at its upper end a male Leur-Lok fitting or other means for attachment of the needle to a syringe as hereinafter explained. The lower end 61 of hub 58 is shaped to fit into and tightly seal against the opening 26 of hub 23. Projecting radially from hub 58 is a vane 62 which is used to orient the position of the curve 55 of needle 56. It also provides a good grip for the surgeon in installing the syringe 66 which has a female Leur-Lok fitting 67 at its lower end which engages fitting 59. The Leur-Lok 59, 68 insures a liquid-tight fit even under extreme pressure for injection of fluids from syringe 66 through needle 56 after the disc has been punctured. In this respect, the connection is superior to that of the stylet and obturator with the cannula 21.

Figure 5:
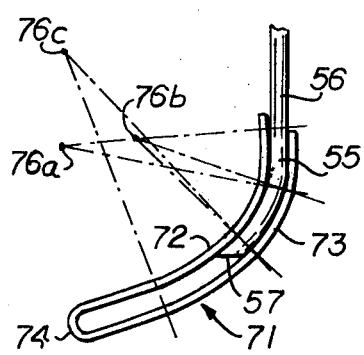
FIG. 5 is a side elevational view of the structure of FIG. 4 showing schematically the centers of radii of curvature of the device.
Figure 4:
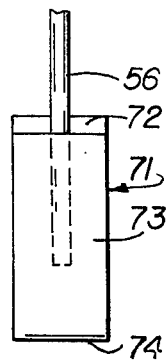
FIG. 4 is a front elevational view of a tool for bending a needle.
Figure 8:
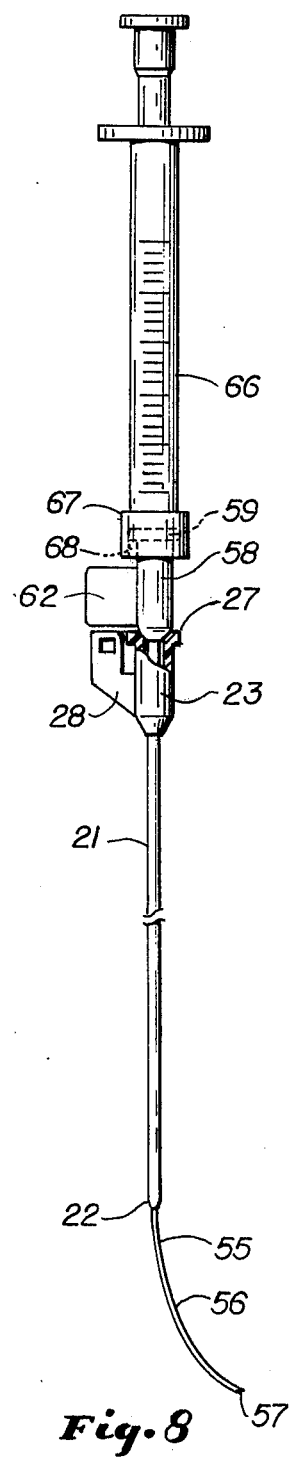
FIG. 8 is a side elevational view partly broken away in section showing the cannula, disc penetration needle and syringe.

It is sometimes desirable to bend the lower end of needle 56 in order to make it possible to maneuver the tip 57 around obstacles. The instrument shown in FIGS. 4 and 5 is useful for bending the needle 56 to form the curve 55. Tool 71 has an inside leaf 72 and substantially parallel to it an outside leaf 73 which are curved and connected together at the lower end as viewed in FIG. 5 by a reverse bend 74. The curvature of leaves 72, 73 is not uniform but rather consists of several sections which have as their center of curvature points 76a, 76b and 76c as shown in FIG. 5, it being understood that other curvatures may be selected. When the needle 56 is inserted between the leaves 72, 73 to the proper distance, the surgeon grips the two leaves together causing the bend 55 to be formed. The extent to which the needle 56 is inserted between the leaves 72, 73 determines the bend which is formed thereon. It will be understood that for each operation and for each needle used in an operation where more than one disc is to be treated, the curvature can be selected for the particular task at hand.

What is claimed is:

1. A cannula comprising a lumen having a central longitudinal bore, a hub on the proximal end of said lumen, a vane extending outward of said bore parallel to said bore formed with an aperture having an axis transverse to said bore, said axis not intersecting said bore.

2. In combination, a cannula according to claim 1 and an instrument having a shaft fitting inside said lumen, and of a length to protrude slightly beyond the end of said cannula, a second hub on said instrument, said second hub shaped to receive said first mentioned hub of said cannula, a hook projecting from said second hub, said hook shaped to fit into said aperture to lock said hubs together in a fixed, predetermined position so that said shaft projects from the end of said cannula.

3. The combination of claim 2 in which said hook is resilient and formed with a barb to latch on said vane.

4. The combination of claim 2 in which said instrument is a stylet having a sharp point.

5. The combination of claim 2 in which said instrument is an obturator.

6. In combination, a cannula according to claim 1 and a disc puncturing needle shaped to fit inside said lumen and to project beyond the end thereof, and a second hub on said needle shaped to engage said first-mentioned hub of said cannula, locking-means on the upper end of said second hub adapted to engage cooperating locking means on the barrel of a conventional syringe of the type formed with said last-named locking means adapted to engage a conventional needle.

7. The combination of claim 6 in which said needle is formed with a bevel and said second hub has a second vane aligned with said bevel.

8. The combination of claim 7 in which said needle projects beyond the distal end of said cannula, said needle curved in alignment with said second vane.

9. A puncturing needle comprising an elongated lumen formed with a bevel at its distal end, a hub on the proximal end of said lumen, said hub having means on its upper end for attachment to a syringe, and a thin vane extending radially from said hub oriented in the same direction as said bevel.

10. A needle according to claim 9 in which the distal end of said lumen is formed with a curve in the direction opposite said vane.

* * * * *